United States Patent
Stack et al.

(10) Patent No.: US 6,821,981 B2
(45) Date of Patent: Nov. 23, 2004

(54) AZAHETEROCYCLYLMETHYL DERIVATIVES OF 2,3-DIHYDRO-1,4-DIOXINO[2,3-F]-QUINOLINE AS 5-HT1A ANTAGONISTS

(75) Inventors: Gary P. Stack, Ambler, PA (US); Megan Tran, Hoboken, NJ (US); Jonathan L. Gross, Robbinsville, NJ (US); George E. M. Husbands, Berwyn, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/131,997

(22) Filed: Apr. 25, 2002

(65) Prior Publication Data

US 2002/0193366 A1 Dec. 19, 2002

Related U.S. Application Data

(60) Provisional application No. 60/286,567, filed on Apr. 26, 2001.

(51) Int. Cl.[7] .................. C07D 491/04; A61K 31/44; A61K 31/335; A61K 25/00
(52) U.S. Cl. .................. 514/278; 514/291; 546/20; 546/90
(58) Field of Search ............... 514/278, 291; 546/20, 90

(56) References Cited

U.S. PATENT DOCUMENTS

| | | | |
|---|---|---|---|
| 3,577,425 A | 5/1971 | Nakanishi et al. | 260/293.4 |
| 5,221,745 A | 6/1993 | Stack | 546/198 |
| 5,318,988 A | 6/1994 | Schohe-Loop et al. | 514/458 |
| 5,371,094 A | 12/1994 | Heine | 514/323 |
| 5,756,532 A | 5/1998 | Stack et al. | 514/411 |
| 5,869,490 A | 2/1999 | Stack | 514/255 |

FOREIGN PATENT DOCUMENTS

| | | |
|---|---|---|
| GB | 1010751 | 11/1965 |
| WO | WO 91/13872 | 9/1991 |
| WO | WO 96/24596 | 8/1996 |

OTHER PUBLICATIONS

Saxena et al. (Pharmac. Ther. vol. 66, pp. 339–368, 1995).*
Robichaud et al. (Annual reports in Medicinal Chemistry 35, Chapter 2) 2000.*
Frederic Saudou et al., Med. Chem. Res., 1994, 16–84, 4.
Michael D. Ennis et al., J. Med. Chem., 1992, 3058–3066, 35.
M. Carli et al., Neuropharmacology, 1999, 1165–1173, 38(8).
Carl Boast et al., Nuerobiol. Learning and Memory, 1999, 259–271, 71(3).
Alfredo Meneses et al., Neurobiol. Learning and Memory, 1999, 207–218, 71(2).

* cited by examiner

*Primary Examiner*—Bruck Kifle
(74) *Attorney, Agent, or Firm*—Woodcock Washburn LLP

(57) ABSTRACT

Compounds of the formula

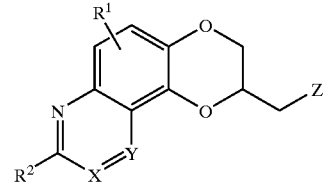

useful for the treatment of disorders, such as anxiety, aggression and stress, and for the control of various physiological phenomena, such as appetite, thermoregulation, sleep and sexual behavior.

37 Claims, No Drawings

AZAHETEROCYCLYLMETHYL DERIVATIVES OF 2,3-DIHYDRO-1,4-DIOXINO[2,3-F]-QUINOLINE AS 5-HT1A ANTAGONISTS

BACKGROUND OF THE INVENTION

This application claims priority from provisional application Ser. No. 60/286,567, filed on Apr. 26, 2001, the entire disclosure of which is hereby incorporated by reference.

Recent studies with the selective $5HT_{1A}$ antagonist WAY-100635 have confirmed a role for $5-HT_{1A}$ receptors in learning and memory. Carli et. al. (Neuropharmacology (1999), 38(8), 1165–1173) demonstrated that WAY-100635 prevented the impairment of spatial learning caused by intrahippocampal injection of 3-[(R)-2-carboxypiperazin-4-yl]propyl-1-phosphonic acid (CPP), a competitive NMDA receptor antagonist, in a two-platform spatial discrimination task. Boast et. al. (Neurobiol. Learn. Mem. (1999), 71(3) 259–271) found that WAY-100635 significantly reduced the cognitive impairment induced by the non-competitive NMDA antagonist MK801, as determined by the performance of rats trained on a delayed nonmatching to sample radial arm maze task. Menesis et. al. (Neurobiol. Learn. Mem. (1999), 71(2) 207–218) showed that post-training administration of WAY-100635 reversed the learning deficit induced by scopolamine, a cholinergic antagonist, in an autoshaping learning task. Novel $5-HT_{1A}$ antagonists would be useful for this and other uses.

DESCRIPTION OF THE INVENTION

In accordance with this invention, there is provided a group of novel compounds of the formula I:

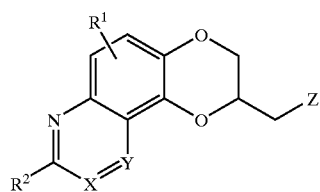

(I)

wherein $R^1$ is hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$ is hydrogen, hydroxy, halo, amino, mono- or di-alkylamino in which each alkyl group has 1 to 6 carbon atoms, or alkyl of one to six carbon atoms;

X is N or $CR^3$;

Y is N or CH;

$R^3$ is hydrogen or alkyl of one to six carbon atoms;

Z is pyrrolidine, piperidine, homopiperidine, morpholine, thiomorpholine,

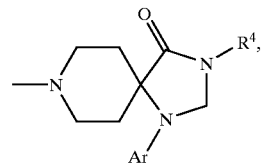

II

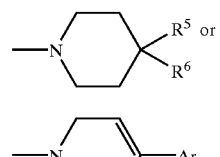

III

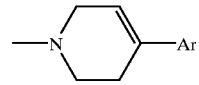

IV $R^4$ is hydrogen, alkyl of 1 to 6 carbon atoms, alkenyl of 3 to 6 carbon atoms or alkynyl or 3 to 6 carbon atoms;

Ar is phenyl, naphthyl, pyridinyl, pyrimidinyl, pyrazinyl, furyl, or thienyl, each optionally substituted;

$R^5$ is hydroxy, cyano or carboxamido and $R^6$ is Ar; or $R^5$ is hydrogen and $R^6$ is benzoyl, 1-benzimidazol-2-one, benzoisothiazole, benzisoxazole, each optionally substituted, or $—(CH_2)_mQ$;

m is 0 to 4; and

Q is Ar,

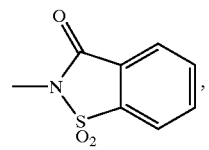

V

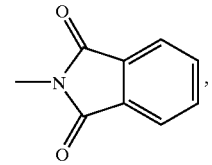

VI

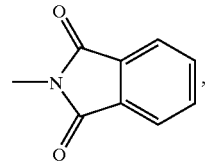

VII

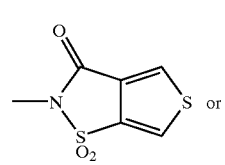

VIII or a pharmaceutically acceptable salt thereof.

In some embodiments of the invention, $R^1$ is hydrogen, halo, trifluoromethyl, alkyl of one to six carbon atoms, alkoxy of one to six carbon atoms, amino, mono- or di-alkylamino in which each alkyl group has one to six carbon atoms. In still more preferred embodiments of the invention $R^1$ is hydrogen, halo, trifluoromethyl, alkyl of one to six carbon atoms or alkoxy of one to six carbon atoms.

In other preferred embodiments of the invention, $R^2$ is hydrogen, amino, mono- or di-alkylamino in which each alkyl group has one to six carbon atoms, or alkyl of one to six carbon atom. In more preferred embodiments of the invention $R^2$ is hydrogen, or alkyl of one to six carbon atom.

X and Y are each preferably each CH.

In some preferred embodiments of the invention, $R^1$ is hydrogen, halo, trifluoromethyl, alkyl of one to six carbon atoms, alkoxy of one to six carbon atoms, amino, mono- or di-alkylamino in which each alkyl group has one to six carbon atoms; $R^2$ is hydrogen, amino, mono- or di-alkylamino in which each alkyl group has one to six carbon atoms, or alkyl of one to six carbon atom, and Z is a radical of formula II.

Still more preferably $R^1$ is hydrogen, halo, trifluoromethyl, alkyl of one to six carbon atoms or alkoxy of one to six carbon atoms; $R^2$ is hydrogen, or alkyl of one to six carbon atom, X and Y are CH, and Z is a radical of formula II.

In other preferred embodiments of the invention, $R^1$ is hydrogen, halo, trifluoromethyl, alkyl of one to six carbon atoms, alkoxy of one to six carbon atoms, amino, mono- or di-alkylamino in which each alkyl group has one to six carbon atoms; $R^2$ is hydrogen, amino, mono- or di-alkylamino in which each alkyl group has one to six carbon atoms, or alkyl of one to six carbon atom, and Z is a radical of formula III, $R^5$ is hydroxy and $R^6$ is Ar; or $R^5$ is hydrogen and $R^6$ is benzoyl, 1-benzimidazol-2-one, benzoisothiazole, benzisoxazole, each optionally substituted, or —$(CH_2)_mQ$ in which m and Q are defined above.

Still more preferably $R^1$ is hydrogen, halo, trifluoromethyl, alkyl of one to six carbon atoms or alkoxy of one to six carbon atoms; $R^2$ is hydrogen, or alkyl of one to six carbon atom, X and Y are CH; Z is a radical of formula III, $R^5$ is hydroxy and $R^6$ is Ar; or $R^5$ is hydrogen and $R^6$ is benzoyl, 1-benzimidazol-2-one, benzoisothiazole, benzisoxazole, each optionally substituted, or —$(CH_2)_mQ$ and m is 0 or 1.

In yet other embodiments of the invention, $R^1$ is hydrogen, halo, trifluoromethyl, alkyl of one to six carbon atoms, alkoxy of one to six carbon atoms, amino, mono- or di-alkylamino in which each alkyl group has one to six carbon atoms; $R^2$ is hydrogen, amino, mono- or di-alkylamino in which each alkyl group has one to six carbon atoms, or alkyl of one to six carbon atom, and Z is a radical of formula IV.

Still more preferably $R^1$ is hydrogen, halo, trifluoromethyl, alkyl of one to six carbon atoms or alkoxy of one to six carbon atoms; $R^2$ is hydrogen, or alkyl of one to six carbon atom, X and Y are CH; and Z is a radical of formula IV.

It is preferred in still other embodiments of the invention that Z is a radical of formula II or III.

Where a substituent is "substituted" as used herein it may include from 1 to 3 substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

This invention relates to both the R and S stereoisomers of the aminomethyl-2,3-dihydro-1,4-dioxino[2,3-f] quinolines, -quinazolines or quinoxalines as well as to mixtures of the R and S stereoisomers. Throughout this application, the name of the product of this invention, where the absolute configuration of the aminomethyl-2,3-dihydro-1,4-dioxino[2,3-f]quinolines, -quinazolines or quinoxalines is not indicated, is intended to embrace the individual R and S enantiomers as well as mixtures of the two. In some preferred embodiments of the present invention the S stereoisomer is preferred.

Where a stereoisomer is preferred, it may, in some embodiments be provided substantially free of the corresponding enantiomer. Thus, an enantiomer substantially free of the corresponding enantiomer refers to a compound which is isolated or separated via separation techniques or prepared free of the corresponding enantiomer. Substantially free, as used herein means that the compound is made up of a significantly greater proportion of one stereoisomer. In preferred embodiments the compound is made up of at least about 90% by weight of a preferred stereoisomer. In other embodiments of the invention, the compound is made up of at least about 99% by weight of a preferred stereoisomer. Preferred stereoisomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, N.Y. 1962); Wilen, S. H. *Tables of Resolving Agents and Optical Resolutions* p. 268 (E. L. Eliel, Ed., Univ. of Notre Dame Press, Notre Dame, Ind. 1972).

Alkyl as used herein refers to an aliphatic hydrocarbon chain and includes straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. Lower alkyl refers to alkyl having 1 to 3 carbon atoms.

Alkanamido as used herein refers to the group R—C(=O)—NH— where R is an alkyl group of 1 to 5 carbon atoms.

Alkanoyloxy as used herein refers to the group R—C(=O)—O— where R is an alkyl group of 1 to 5 carbon atoms.

Alkanesulfonamido as used herein refers to the group R—S(O)$_2$—NH— where R is an alkyl group of 1 to 6 carbon atoms.

Alkoxy as used herein refers to the group R—O— where R is an alkyl group of 1 to 6 carbon atoms.

Carboxamido as used herein refers to the group —CO—NH$_2$.

Carboalkoxy as used herein refers to the group R—O—C(=O)— where R is an alkyl group of 1 to 5 carbon atoms.

Halogen (or halo) as used herein refers to chlorine, bromine, fluorine and iodine.

Pharmaceutically acceptable salts are those derived from such organic and inorganic adds as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Specific compounds of the present invention are:

8-[2,3-dihydro[1,4]dioxino[2,3-f]quinolin-2-ylmethyl]-1-phenyl-1,3,8-triazaspiro[4,5]decan-4-one;

8-{[8-methyl-2,3-dihydro[1,4]dioxino[2,3-f]quinolin-2-yl]methyl}-1-phenyl-1,3,8-triazaspiro[4,5]decan-4-one;

1-(1-{[8-methyl-2,3-dihydro[1,4]dioxino[2,3-f]quinolin-2-yl]methyl}-piperidin-4-yl)-1,3-dihydro-2H-benzimidazol-2-one;

8-methyl-2-(piperidin-1-ylmethyl)-2,3-dihydro[1,4]dioxino[2,3-f]quinoline;
(4-fluorophenyl)(1-{[8-methyl-2,3-dihydro[1,4]dioxino[2,3-f]quinolin-2-yl]methyl}-4-piperidinyl)methanone;
1-{[8-methyl-2,3-dihydro[1,4]dioxino[2,3-f]quinolin-2-yl]methyl}-4-[3-(trifluoromethyl)phenyl]-4-piperidinol;
1-{[8-methyl-2,3-dihydro[1,4]dioxino[2,3-f]quinolin-2-yl]methyl}-4-phenyl-4-piperidinecarbonitrile;
8-methyl-2-{[4-phenyl-3,6-dihydro-1(2H)-pyridinyl]methyl}-2,3-dihydro[1,4]dioxino[2,3-f]quinoline;
8-{[8-ethyl-2,3-dihydro[1,4]dioxino[2,3-f]quinolin-2-yl]methyl}-1-phenyl-1,3,8-triazaspiro[4.5]decan-4-one; or pharmaceutically acceptable salts thereof.

The 2-azaheterocyclylmethyl-2,3-dihydro-1,4-dioxino[2,3-f]quinolines in which $R^2$ is H are prepared as illustrated below. Specifically, the appropriately substituted nitroguaiacol is alkylated with allyl bromide in the presence of a suitable base such as sodium hydride and then demethylated by a reagent such as sodium hydroxide. The resulting 4-nitro-2-allyloxyphenol is then alkylated with glycidyl

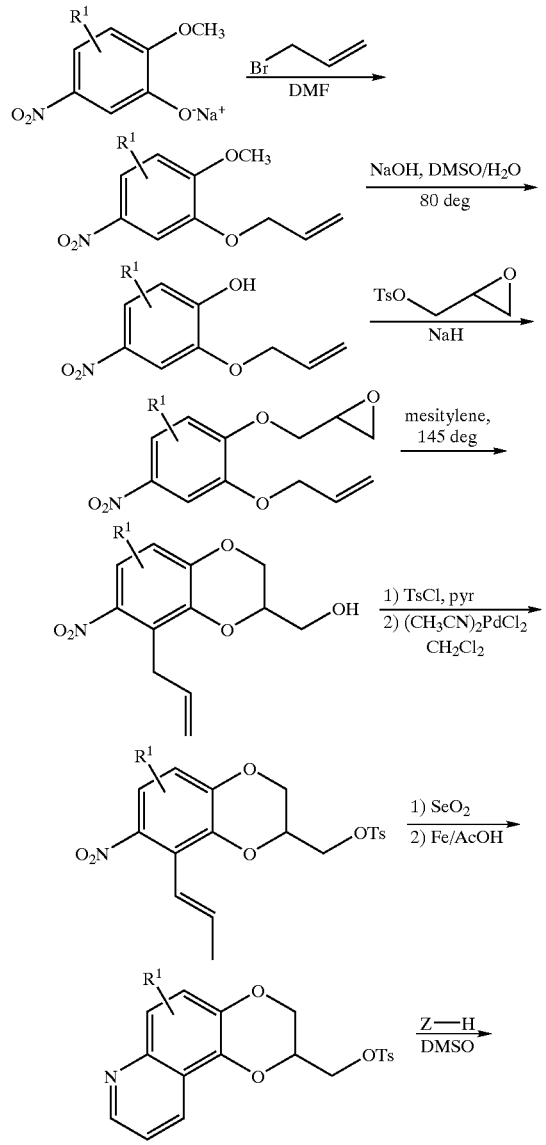

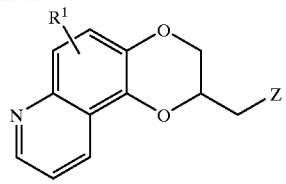

tosylate or an epihalohydrin in the presence of a base such as sodium hydride and heated in a high boiling solvent such as mesitylene or xylene to effect both rearrangement of the allyl group and cyclization of the dioxan ring. The resulting primary alcohol is converted to the tosylate by reaction with p-toluenesulfonyl chloride in the presence of a tertiary amine or pyridine, or alternatively to a halide by reaction with carbon tetrabromide or carbon tetrachloride in combination with triphenylphosphine. The allyl side chain is then isomerized by treatment with catalytic bis-acetonitrile palladium (II) chloride in refluxing methylene chloride or benzene. Allylic oxidation with selenium dioxide in refluxing dioxane/water gives the o-nitrocinnamaldehyde, which upon reduction with iron in acetic acid cyclizes to the 2,3-dihydro-1,4-dioxino[2,3-f]quinoline-2-methyltosylate or halide. Replacement of the tosylate or halide with the appropriately substituted azaheterocycle (Z—H) in some high boiling solvent such as dimethyl sulfoxide gives the title compounds of the invention.

The 2-azaheterocyclylmethyl-2,3-dihydro-1,4-dioxino[2,3-f]quinolines of the invention in which $R^2$ is alkyl may be prepared from the nitro olefin described above in the following manner. The rearranged olefin is treated sequentially with ozone and a tertiary amine or with osmium tetroxide and sodium periodate to give the O-nitrobenzaldehyde. Condensation with the appropriate

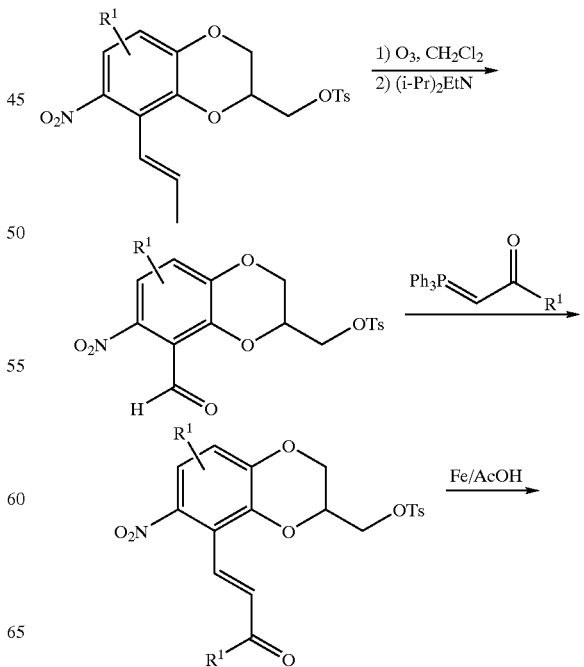

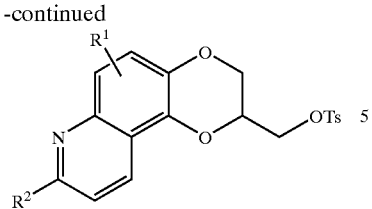

triphenylphosphoranylidene ketone under Wittig conditions gives the o-nitrostyryl ketone, which upon reduction by iron in acetic acid, cyclizes to the corresponding 2,3-dihydro-1,4-dioxino[2,3-f]quinoline-2-methyltosylate. Replacement of the tosylate with the appropriately substituted azaheterocycle as above gives the title compounds of the invention. Substitution of trimethyl phosphonoacetate for the triphenylphosphoranylidene ketone in the Wittig procedure above, followed by reduction of the nitro group with tin (II) chloride and cyclization in acid gives the compounds of the invention in which $R^2$ is hydroxy. Alkylation of this hydroxy derivative by a suitable alkyl halide or tosylate in the presence of base gives the compounds of the invention in which $R^2$ is alkoxy. Treatment of the hydroxy derivative with an inorganic acid chloride such as phosphoryl chloride or bromide gives the compounds of the invention in which $R^2$ is halo. Substitution of diethyl cyanomethylphosphonate for the triphenylphosphorylidene ketone in the Wittig procedure above, followed by reduction of the nitro group with tin (II) chloride and cyclization in acid gives the compounds of the invention in which $R^2$ is amino.

Compounds of the invention in which $R^1$ is attached to position 6 of the 2,3-dihydro-1,4-dioxino[2,3-f]quinoline may be alternatively prepared by a variation of the Skraup quinoline synthesis according to the scheme below. The appropriately substituted benzodioxan methyltosylate is nitrated under standard conditions with nitric acid in a solvent such as dichloroethane and the resulting nitro

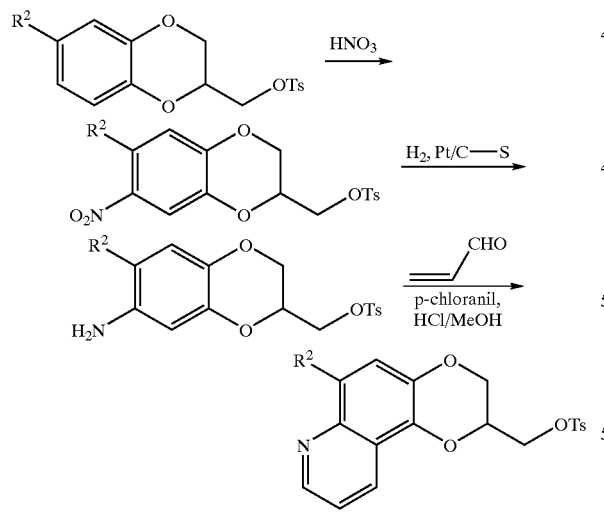

compound reduced by treatment with hydrogen in the presence of a catalyst such as platinum on sulfide carbon. Treatment of the resulting aniline with acrolein in the presence of hydrogen chloride and an oxidant such as p-chloranil or naphthoquinone gives the corresponding 2,3-dihydro-1,4-dioxino[2,3-f]quinoline. Replacement of the tosylate with the appropriately substituted azaheterocycle as above gives the title compounds of the invention.

The 2-azaheterocyclylmethyl-2,3-dihydro-1,4-dioxino[2,3-f]quinazolines of the invention are prepared as illustrated below. The o-nitrobenzaldehyde described above is converted to the oxime by

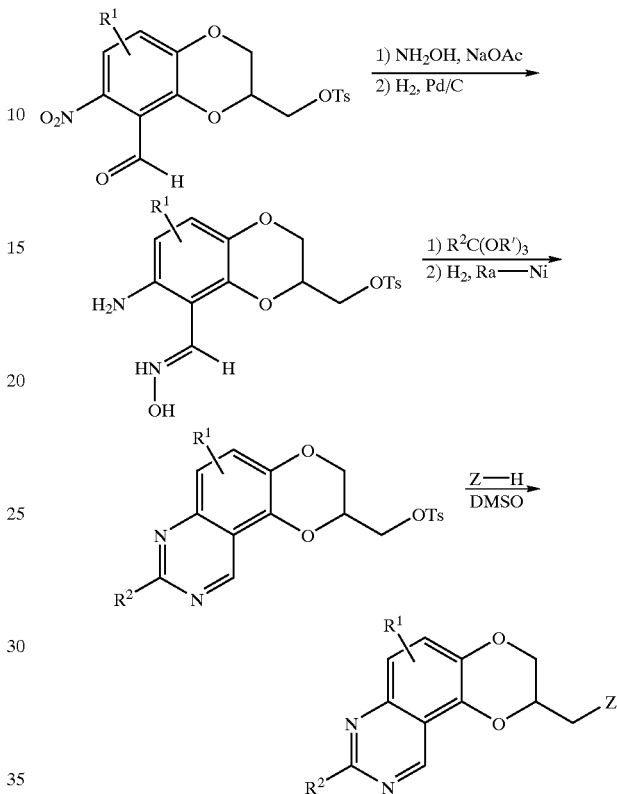

treatment with hydroxylamine hydrochloride in the presence of a suitable base such as sodium acetate and the nitro group reduced to the amine by hydrogenation over palladium on carbon. Cyclization to the quinazoline N-oxide is effected by treatment at reflux with the appropriate ortho ester according to the method of Ostrowski (Heterocycles, vol. 43, No. 2, p. 389, 1996). The quinazoline N-oxide may be reduced to the quinazoline by a suitable reducing agent such as hydrogen over Raney-nickel. Alternatively, an extended period of reflux in the ortho ester gives the reduced quinazoline directly via a disproportionation reaction and the 2,3-dihydro-1,4-dioxino[2,3-f]quinazoline-2-methyltosylate or halide may be isolated by column chromatography. Replacement of the tosylate or halide with the appropriately substituted azaheterocycle in some high boiling solvent such as dimethyl sulfoxide gives the title compounds of the invention.

The 2-azaheterocyclylmethyl-2,3-dihydro-1,4-dioxino[2,3-f]quinoxalines of the invention are prepared as illustrated below. The o-nitrobenzaldehyde described above is oxidized to the o-nitrobenzoic acid by a suitable oxidant such as chromium trioxide (Jones' oxidation) or sodium chlorite and the acid converted to the o-nitroaniline with diphenylphosphoryl azide (DPPA) in the presence of a tertiary base such as diisopropylethylamine. Reduction of the resulting nitroaniline to the diamine with hydrogen and

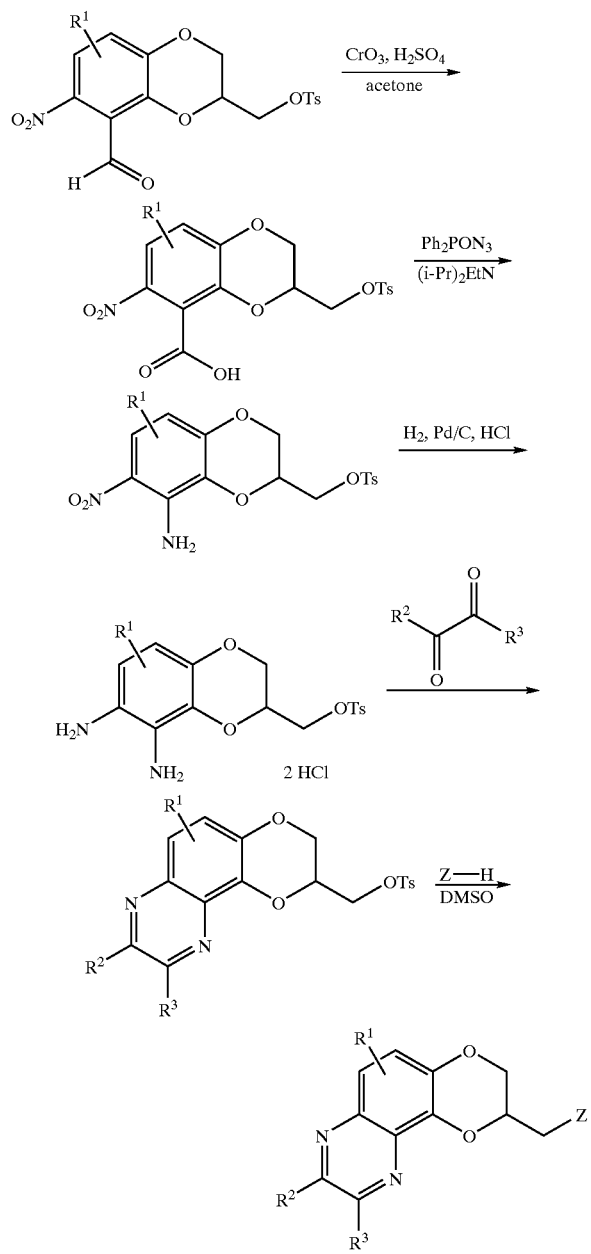

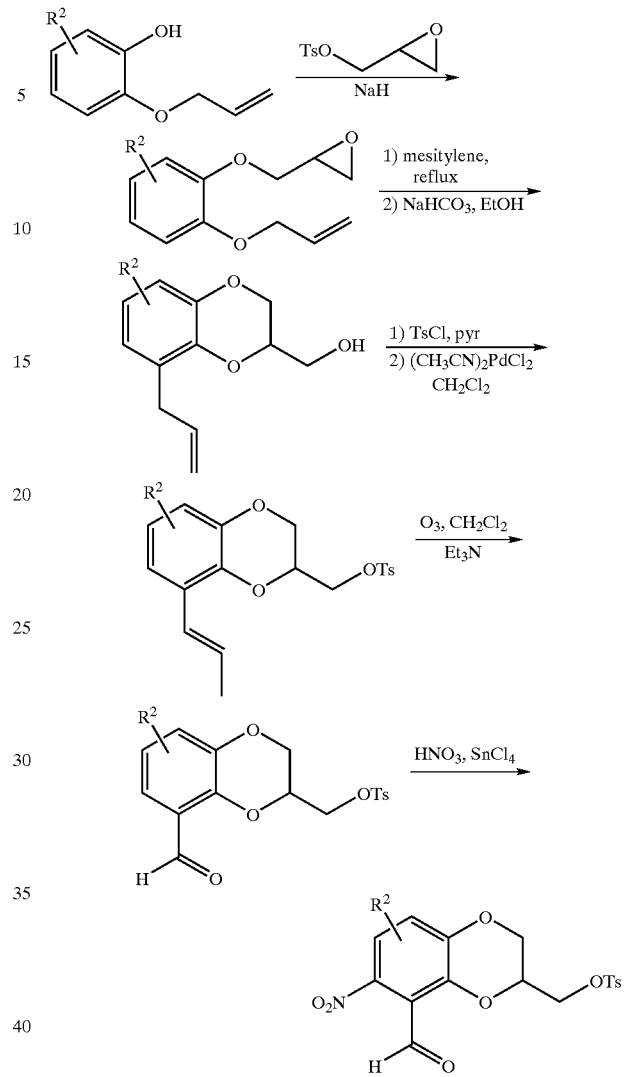

palladium on carbon and cyclization by treatment with the appropriate dicarbonyl compound (for example, glyoxal, 2,3-butanedione, 3,4-hexanedione) gives the 2,3-dihydro-1,4-dioxino[2,3-f]quinoxaline-2-methyltosylate or halide. Replacement of the tosylate or halide with the appropriately substituted azaheterocycle in some high boiling solvent such as dimethyl sulfoxide gives the title compounds of the invention.

The o-nitrobenzaldehyde used in the chemistry described above may be alternatively prepared as shown below. The appropriate mono-allylated catechol is elaborated with glycidyl tosylate as described above and rearranged in refluxing mesitylene. Cyclization to the benzodioxan methanol is effected by treatment with sodium bicarbonate in ethanol and the alcohol is converted to the tosylate or halide as described above. After rearrangement of the double bond by treatment with catalytic bis-acetonitrile palladium (II) chloride in refluxing methylene chloride and cleavage with ozone or osmium tetroxide/sodium periodate as described above, the resulting aldehyde is regioselectively nitrated with a combination of nitric acid and tin (IV) chloride.

The guaiacols, catechols, benzodioxan methyltosylates and azaheterocycles appropriate to the above chemistry are known compounds or can be prepared by one schooled in the art. The compounds of the invention may be resolved into their enantiomers by conventional methods or, preferably, the individual enantiomers may be prepared directly by substitution of (2R)-(−)-glycidyl 3-nitrobenzenesulfonate or tosylate (for the S benzodioxan methanamine) or (2S)-(+)-glycidyl 3-nitrobenzenesulfonate or tosylate (for the R enantiomer) in place of epihalohydrin or racemic glycidyl tosylate in the procedures above.

High affinity for the serotonin 5-$HT_{1A}$ receptor was established by testing the claimed compound's ability to displace [$^3$H] 8-OH-DPAT (dipropylaminotetralin) from the 5-$HT_{1A}$ serotonin receptor following a modification of the procedure of Hall et al., J. Neurochem. 44, 1685 (1985) which utilizes CHO cells stably transfected with human 5-$HT_{1A}$ receptors.

The 5-HT$_{1A}$ affinities for the compounds of the invention are reported below as K$_i$'s.

Antagonist activity at 5-HT$_{1A}$ receptors was established by using a $^{35}$S-GTPγS binding assay similar to that used by Lazareno and Birdsall (Br. J. Pharmacol. 109: 1120, 1993), in which the test compound's ability to affect the binding of $^{35}$S-GTPγS to membranes containing cloned human 5-HT$_{1A}$ receptors was determined. Agonists produce an increase in binding whereas antagonists produce no increase but rather reverse the effects of the standard agonist 8-OH-DPAT. The test compound's maximum inhibitory effect is represented as the I$_{max}$, while its potency is defined by the IC$_{50}$.

The results of the two standard experimental test procedures described in the preceding two paragraphs were as follows:

| Compound | 5-HT$_{1A}$ Receptor Affinity KI (nM) | 5-HT$_{1A}$ Function IC$_{50}$ (nM) (I$_{max}$) |
|---|---|---|
| Example 1 | 1.44 | 55.0 (100) |
| Example 2 | 1.79 | 64.0 (100) |
| Example 3 | 3.08 | 66.0 (85.0) |
| Example 4 | 51.04 | 483.0 (100) |
| Example 5 | 18.53 | |
| Example 6 | 6.94 | |
| Example 7 | 76.08 | 444.90 (50) |
| Example 8 | 7.91 | |
| Example 9 | 2.79 | |

The compounds of this invention have potent affinity for and antagonist activity at brain 5-HT$_{1A}$ serotonin receptors. The compounds of the invention are thus exceedingly interesting for the treatment of cognitive dysfunction such as is associated with mild cognitive impairment (MCI) Alzheimer's disease and other dementias including Lewy Body, vascular, and post stroke dementias. Cognitive dysfunction associated with surgical procedures, traumatic brain injury or stroke may also be treated in accordance with the present invention. Further, compounds of the present invention may be useful for the treatment of diseases in which cognitive dysfunction is a co-morbidity such as, for example, Parkinson's disease, autism and attention deficit disorders.

Compounds of the present invention are also useful for treating cognitive deficits due to CNS disorders such as schizophrenia, (and other psychotic disorders such as paranoia and mano-depressive illness). The compounds are also useful for the treatment of disorders related to excessive serotonergic stimulation such as anxiety (e.g. generalized anxiety disorders, panic attacks, and obsessive compulsive disorders), aggression and stress. In addition, compounds of the present invention may be useful for the treatment of various physiological conditions such as Tourette's syndrome, migraine, autism, attention deficit disorders and hyperactivity disorders, sleep disorders, social phobias, pain, thermoregulatory disorders, endocrine disorders, urinary incontinence, vasospasm, stroke, eating disorders such as for example obesity, anorexia and bulimia, sexual dysfunction, and the treatment of alcohol, drug and nicotine withdrawal which are known to be, at least in part, under serotonergic influence. Finally, recent clinical trials employing drug mixtures (e.g. fluoxetine and pindolol) have demonstrated a more rapid onset of antidepressant efficacy for a treatment combining SSRI (serotonin selective reuptake inhibitor) activity and 5HT1A antagonism (Blier and Bergeron, 1995; F Artigas, et al., 1996, M. B. Tome et al., 1997). The compounds of the invention are thus interesting and useful as augmentation therapy in the treatment of depressive illness.

Thus the present invention provides methods of treating, preventing, inhibiting or alleviating each of the maladies listed above in a mammal, preferably in a human, the methods comprising providing a pharmaceutically effective amount of a compound of this invention to the mammal in need thereof.

The present invention also provides methods of augmenting the treatment of depression by providing a mammal, preferably a human with an antidepressant amount of a serotonin selective reuptake inhibitor (such as, but not limited to, sertraline, fluvoxamine, paroxetine, citalopram, fluoxetine and metabolites thereof) and an amount of a compound of Formula I sufficient to hasten the onset of antidepressant efficacy.

Also encompassed by the present invention are pharmaceutical compositions for treating or controlling disease states or conditions of the central nervous system comprising at least one compound of Formula I, mixtures thereof, and or pharmaceutical salts thereof, and a pharmaceutically acceptable carrier therefore. Such compositions are prepared in accordance with acceptable pharmaceutical procedures, such as described in Remingtons Pharmaceutical Sciences, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

Compounds of the present invention may further be provided in combination with an antidepressant amount of a serotonin selective reuptake inhibitor to increase the onset of antidepressant efficacy.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of the present invention are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age and response pattern of the patient. Generally, a starting dose is about 10 mg per day with gradual increase in the daily dose to about 200 mg per day, to provide the desired dosage level in the human.

Provide, as used herein, means either directly administering a compound or composition of the present invention, or administering a prodrug, derivative or analog which will form an equivalent amount of the active compound or substance within the body.

The present invention includes prodrugs of compounds of Formula I. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991), Bundgaard, et al., Journal of Drug Deliver Reviews, 8:1–38(1992), Bundgaard, J. of Pharmaceutical Sciences, 77:285 et seq. (1988); and Higuchi and Stella (eds.) Prodrugs as Novel Drug Delivery Systems, American Chemical Society (1975).

The following examples illustrate the production of representative compounds of this invention.

INTERMEDIATE 1

3-Allyloxy-4-methoxynitrobenzene 97.5 g (0.51 mole) of the sodium salt of 5-nitroguaiacol was dissolved in one liter of DMF and 1.5 equivalents of allyl bromide added. The reaction was heated to 65° C. for two hours, after which time much of the dark color had discharged and tlc (1:1 $CH_2Cl_2$/hexane) indicated loss of starting material. The solvent was concentrated in vacuum and the residue washed with water. The product was isolated by filtration and dried in a vacuum. This gave 112 g of pale yellow solid. A sample recrystallized from methanol, gave m.p. 93–94° C.

INTERMEDIATE 2

2-Allyloxy-4-nitrophenol

To one liter of dimethyl sulfoxide was added 750 mL of 2 N aqueous sodium hydroxide and the mixture was heated to 65° C. The pale yellow solid 3-allyloxy-4-methoxynitrobenzene prepared above was added in portions over a 30 minute period and then the temperature was raised to 95° C. and maintained for 3 hours, after which time the starting material had been consumed. The mixture was allowed to cool and poured into a mixture of 1 L ice and 1 L 2 N HCl. 73 Grams of crude but homogeneous (by tlc 1:1 $CH_2Cl_2$/hexane) desired product was isolated as a light brown solid by filtration. This material was subsequently dissolved in 1:1 hexane/methylene chloride and filtered through silica gel to give 68 g of pale yellow solid, which, when recrystallized from ethyl/acetate/hexane, gave m.p. 61–62° C. The aqueous mother liquors from the initial crystallization above were extracted with 2 L of ethyl acetate. This was dried over sodium sulfate, filtered and evaporated to a dark oil. Column chromatography on silica with 1:1 $CH_2Cl_2$/hexane gave an additional 12 g of the title compound as a yellow solid. Elution with 2% MeOH in $CHCl_3$ gave 12 g of a dark oil which slowly crystallized in vacuum. This proved to be the Claisen product, 3-allyl-4-nitrocatechol.

INTERMEDIATE 3

2-(2-Allyoxy-4-nitrophenoxymethyl)-oxirane 20 g (0.50 mole) of 60% NaH/mineral oil was placed in a two liter flask and washed with 500 mL of hexane. 1 L of DMF was added, followed by 77 g (0.40 mole) of the 2-allyloxy-4-nitrophenol prepared in the previous step. Addition of the phenol was performed in portions under argon. After stirring the mixture for 30 minutes at room temperature under argon, 108 g (0.48 moles) of (R)-glycidyl tosylate was added and the mixture heated at 70–75° C. under nitrogen overnight. Upon cooling, the DMF was removed in vacuum and replaced with one liter of methylene chloride. This was washed with 500 mL portions of 2 N HCl, saturated sodium bicarbonate and saturated brine and dried over sodium sulfate. The mixture was filtered, concentrated to an oil in vacuum and column chromatographed on silica gel using 1:1 hexane/methylene chloride as eluant. This gave 43 g of product contaminated with traces of the two starting materials, followed by 21 g of pure product as a pale yellow solid. The impure material was recrystallized from 1.2 L of 10% ethyl acetate/hexane to give 34 g of pure (homogeneous on silica gel tlc with 1:1 hexane/methylene chloride) (R)-2-(2-allyloxy-4-nitrophenoxymethyl)-oxirane (m.p. 64° C.).

Elemental Analysis for: $C_{12}H_{13}NO_5$ Calc'd: C, 57.37; H, 5.21; N, 5.58. Found: C, 57.50; H, 5.21; N, 5.43.

INTERMEDIATE 4

(8-Allyl-7-nitro-2,3-dihydro-benzo(1,4)dioxin-2-yl)-methanol (R)-2-(2-Allyloxy-4-nitrophenoxymethyl)-oxirane (20 g, 80 mmoles) prepared as above was heated at 155° C. in mesitylene for 24 hours under nitrogen. Filtration of the black solid which formed gave 1.5 g of very polar material. Evaporation of the solvent in vacuum followed by column chromatography on silica gel with methylene chloride as eluant gave 10 g of recovered starting material and 7.5 g of the desired rearranged (S)-(8-allyl-7-nitro-2,3-dihydro-benzo(1,4)dioxin-2-yl)-methanol, which slowly crystallized on standing in vacuum (m.p. 67° C.). The yield based on recovered starting material is 75%.

Elemental Analysis for: $C_{12}H_{13}NO_5$ Calc'd: C, 57.37; H, 5.21; N, 5.58. Found: C, 57.26; H, 5.20; N, 5.35.

INTERMEDIATE 5

Toluene-4-sulfonic acid 8-allyl-7-nitro-2,3-dihydro-benzo(1,4)dioxin-2-ylmethyl ester 9.55 g (38.0 mmole) of (S)-(8-allyl-7-nitro-2,3-dihydro-benzo(1,4)dioxin-2-yl)-methanol was dissolved in 465 mL of pyridine, 29.0 g (152 mmole) of p-toluenesulfonyl chloride was added and the mixture stirred at room temperature under nitrogen overnight. Water was then added to quench the excess tosyl chloride and the solvent was removed in vacuum and replaced with methylene chloride. This solution was washed with 2 N HCl, with saturated sodium bicarbonate, and with saturated brine, and dried over magnesium sulfate. Filtration, evaporation in vacuum and column chromatography on silica gel with 1:1 hexane/methylene chloride as eluant gave 12.6 g (92%) of toluene-4-sulfonic acid (R)-allyl-7-nitro-2,3-benzo(1,4)dioxin-2-ylmethyl ester, which slowly crystallized to a tan solid (m.p. 60–62° C.) upon standing.

Elemental Analysis for: $C_{19}H_{19}NO_7S$ Calc'd: C, 56.29; H, 4.72; N, 3.45. Found: C, 56.13; H, 4.58; N, 3.44.

INTERMEDIATE 6

{7-Nitro-8-[1-propenyl]-2,3-dihydro-1,4-benzodioxin-2-yl}methyl 4-methylbenzenesulfonate To a solution of 10.0 g (24.0 mmole) of (R)-[8-allyl-7-nitro-2,3-dihydro-1,4-benzodioxin-2-yl]methyl 4-methylbenzenesulfonate in 700 mL of benzene was added 1.03 g of bis(acetonitrile)dichloropalladium (II) and the mixture was refluxed under nitrogen for 48 hours. The catalyst was then removed by filtration and the filtrate concentrated in vacuum to a brown oil. Column chromatography on silica gel with methylene chloride as eluant gave 7.2 g of the title compound as a mixture of E and Z isomers. A sample of {(2R)-7-nitro-8[(E)-1-propenyl]-2,3-dihydro-1,4-benzodioxin-2-yl}methyl 4-methylbenzenesulfonate was obtained as a yellow solid (m.p. 105–106° C.) by evaporation of a pure E isomer-containing fraction.

Elemental Analysis for: $C_{19}H_{19}NO_7S$ Calc'd: C, 56.29; H, 4.72; N, 3.45. Found: C, 56.12; H, 4.64; N, 3.39.

INTERMEDIATE 7

{7-Nitro-8-[3-oxo-1-propenyl]-2,3-dihydro-1,4-benzodioxin-2-yl}methyl 4-methylbenzenesulfonate {(2R)-7-nitro-8-[1-propenyl]-2,3-dihydro-1,4-benzodioxin-2-yl}methyl 4-methylbenzenesulfonate (6.15 g, 15.2 mmole) was dissolved in 180 mL of dioxane. Selenium dioxide (4.20 g, 37.9 mmole) was then added, followed by 0.70 mL of water. The heterogeneous mixture was heated at reflux under nitrogen for 5 hours. Upon cooling, the reaction was filtered and concentrated in vacuum to yield a dark yellow solid. This was dissolved in minimal ethyl acetate and column chromatographed on silica gel using 30% ethyl acetate in hexane as eluant to give 5.75 g of the (R)-enantiomer of the title compound as a light yellow solid (m.p. 138–140° C.).

Elemental Analysis for: $C_{19}H_{17}NO_8S$ Calc'd: C, 54.41; H, 4.09; N, 3.34. Found: C, 54.10; H, 3.85; N, 3.31.

INTERMEDIATE 8

2,3-Dihydro[1,4]dioxino[2,3-f]quinolin-2-ylmethyl 4-methylbenzenesulfonate

To a solution of {(2R)-7-nitro-8-[3-oxo-1-propenyl]-2,3-dihydro-1,4-benzodioxin-2-yl}methyl 4-methylbenzenesulfonate (3.50 g, 8.35 mmole) in 200 mL of acetic acid/ethanol (1:1) was added 2.35 g (42.1 mmole) of iron powder and the mixture was heated at reflux under nitrogen for 8 hours. After the reaction was complete, 150 mL of water was added and the mixture filtered through a pad of celite. The filtrate was neutralized with saturated sodium bicarbonate and extracted with ethyl acetate. The extract was dried over magnesium sulfate, filtered and evaporated in vacuum. The residue was column chromatographed on silica gel using a gradient elution commencing with 20% ethyl acetate/hexane and ending with 70% ethyl acetate/hexane to give 1.85 g of the (R)-enantiomer of the title compound as a yellow oil. $^1$H-NMR (CDCl$_3$): doublet 8.8 δ (1 H); doublet 8.2 δ (1 H); doublet 7.8 δ (2 H); doublet 7.6 δ (1 H); multiplet 7.35 δ (1 H); multiplet 7.25 δ (3 H); multiplet 4.6 δ (1 H); multiplet 4.3–4.4 δ (3 H); multiplet 4.2 δ (1 H); singlet 2.4 δ (3 H).

EXAMPLE 1

8-[2,3-Dihydro[1,4]dioxino[2,3-f]quinolin-2-ylmethyl]-1-phenyl-1,3,8-triazaspiro[4.5]decan-4-one (2R)-2,3-Dihydro[1,4]dioxino[2,3-f]quinolin-2-ylmethyl 4-methylbenzenesulfonate (0.41 g, 1.1 mmole) and 1-phenyl-1,3,6-triazaspiro[4.5]decan-4-one (0.75 g, 3.24 mmole) were combined in 30 mL of DMSO and heated at 80° C. under nitrogen for 6 hours. After cooling to room temperature, the mixture was partitioned between 400 mL each of ethyl acetate and saturated sodium bicarbonate solution. The organic phase was removed, washed with saturated brine, dried over magnesium sulfate and concentrated to a brown oil in vacuum. This was column chromatographed on silica gel using a gradient elution commencing with methylene chloride and ending with 3% methanol in methylene chloride to elute the product, 0.30 g of a reddish oil. The oil was recrystallized from ethanol with the addition of 0.12 g of fumaric acid to give 0.22 g of the (S)-enantiomer of the title compound as a yellow solid difumarate, m.p. 170° C.

Elemental Analysis for: $C_{25}H_{26}N_4O_3 \cdot 2\ C_4H_4O_4$ Calc'd: C, 59.81; H, 5.17; N, 8.45. Found: C, 59.88; H, 5.44; N, 8.38.

INTERMEDIATE 9

(8-Formyl-7-nitro-2,3-dihydro-1,4-benzodioxin-2-yl)methyl 4-methylbenzenesulfonate {(2R)-7-Nitro-8-[1-propenyl]-2,3-dihydro-1,4-benzodioxin-2-yl}methyl 4-methylbenzenesulfonate (10.5 g, 25.9 mmole) dissolved in 400 mL of methylene chloride was treated with excess ozone at −78° C. Diisopropylethylamine (11.5 mL, 66.0 mmole) was then added dropwise over 30 minutes and the mixture allowed to come to room temperature and stir overnight under a nitrogen atmosphere. The mixture was then diluted to 600 mL with methylene chloride, washed three times with 100 mL portions of 2N HCl (aq), twice with 200 mL portions of saturated aqueous sodium bicarbonate and with 200 mL of saturated brine. The solution was dried over magnesium sulfate, filtered and concentrated in vacuum to a crude brown oil, which was column chromatographed on silica gel with 10% hexane/methylene chloride to give 7.52 g of the (R)-enantiomer of the title compound as a yellow solid. $^1$H-NMR (CDCl$_3$): doublet 7.8 δ (2 H); doublet 7.62 δ (1 H); doublet 7.4 δ (2 H); doublet 7.0 δ (1 H); multiplet 4.4–4.6 δ (2 H); multiplet 4.2 δ (3 H); singlet 2.4 δ (3 H).

INTERMEDIATE 10

{7-Nitro-8-[(E)-3-oxo-1-butenyl]-2,3-dihydro-1,4-benzodioxin-2-yl}methyl 4-methylbenzenesulfonate To a solution of 3.00 g (7.37 mmole) of [(2R)-8-formyl-7-nitro-2,3-dihydro-1,4-benzodioxin-2-yl]methyl 4-methylbenzenesulfonate in 250 mL of toluene was added 2.90 g (9.10 mmole) of 1-triphenylphosphoranylidene-2-propanone. The mixture was stirred at room temperature under nitrogen for 5 hours, during which time some product precipitated from solution. The solvent was removed in vacuum and the crude residue was column chromatographed on silica gel with methylene chloride as eluant to give 3.0 g of the (R)-enantiomer of the title compound as a yellow solid. $^1$H-NMR (CDCl$_3$): doublet 7.8 δ (2 H); doublet 7.6 δ (1 H); doublet 7.5 δ (2 H); doublet 7.4 δ (2 H); doublet 6.95 δ (1 H); doublet 6.6 δ (1 H); multiplet 4.5 δ (1 H); doublet of doublets 4.0 δ (1 H); multiplet 4.2 δ (3 H); singlet 2.45 δ (3 H); singlet 2.4 δ (3 H).

INTERMEDIATE 11

(8-Methyl-2,3-dihydro[1,4]dioxino[2,3-f]quinolin-2-yl)methyl 4-methylbenzenesulfonate To a solution of {(2R)-7-nitro-8-[(E)-3-oxo-1-butenyl]-2,3-dihydro-1,4-benzodioxin-2-yl}methyl 4-methylbenzenesulfonate (3.40 g, 7.83 mmole) in 200 mL of acetic acid/ethanol (3:2) was added 2.25 g (40.2 mmole) of iron powder and the mixture was heated at reflux under nitrogen for 8 hours. After the reaction was complete, 150 mL of water was added and the mixture filtered through a pad of celite. The filtrate was neutralized with saturated aqueous sodium bicarbonate and extracted with ethyl acetate. The extract was dried over magnesium sulfate, filtered and evaporated in vacuum. The residue was column chromatographed on silica gel using a gradient elution commencing with 20% ethyl acetate/hexane and ending with 70% ethyl acetate/hexane to give 2.5 g of the (R)-enantiomer of the title compound as a yellow oil. $^1$H-NMR (CDCl$_3$): doublet 8.1 δ (1 H); doublet 7.6 δ (2 H); doublet 7.45 δ (1 H); multiplet 7.2 δ (4 H); multiplet 4.6 δ (1 H); multiplet 4.3 δ (3 H); multiplet 4.1 δ (1 H); singlet 2.5 δ (3H); singlet 2.4 δ (3 H).

EXAMPLE 2

8-{[8-Methyl-2,3-dihydro[1,4]dioxino[2,3-f]quinolin-2-yl]methyl}-1-phenyl-1,3,8-triazaspiro[4.5]decan-4-one (2R)-8-Methyl-2,3-dihydro[1,4]dioxino[2,3-f]quinolin-2-ylmethyl 4-methylbenzenesulfonate (0.75 g, 2.0 mmole) and 1-phenyl-1,3,6-triazaspiro[4.5]decan-4-one (0.92 g, 4.0 mmole) were combined in 10 mL of DMSO and heated at 80° C. under nitrogen for 6 hours. After cooling to room temperature, the mixture was partitioned between 400 mL of ethyl acetate and 250 mL of saturated sodium bicarbonate solution. The organic phase was removed, washed with 250 mL of water, dried over sodium sulfate, filtered and concentrated in vacuum. The residue was column chromatographed on silica gel using 1% methanol in chloroform as eluant to give 0.29 g of a yellow oil. The oil was recrystallized from ethanol with the addition of one equivalent of fumaric acid to give 0.21 g of the (S)-enantiomer of the title compound as a gray solid hemifumarate, hydrate, m.p. 199–201° C.

Elemental Analysis for: C$_{26}$H$_{28}$N$_4$O$_3$.0.5 C$_4$H$_4$O$_4$.H$_2$O Calc'd: C, 64.60; H, 6.20; N, 10.76. Found: C, 64.51; H, 5.89; N, 10.66.

EXAMPLE 3

1-(1-{[8-Methyl-2,3-dihydro[1,4]di xino[2,3-f]quin lin-2-yl]methyl}piperidin-4-yl)-1,3-dihydro-2H-benzimidazol-2-one (2R)-8-Methyl-2,3-dihydro[1,4]dioxino[2,3-f]quinolin-2-ylmethyl 4-methylbenzenesulfonate (0.75 g, 2.0 mmole) and 4-(2-keto-1-benzimidazolinyl)-piperidine (1.0 g, 4.6 mmole) were combined in 10 mL of DMSO and heated at 90–100° C. under nitrogen for 6 hours. After cooling to room temperature, the mixture was partitioned between 400 mL of ethyl acetate and 400 mL of saturated sodium bicarbonate solution. The organic phase was removed, washed with 400 mL of water, dried over sodium sulfate, filtered and concentrated in vacuum. The residue was column chromatographed on silica gel using 1% methanol in chloroform as eluant to give 0.59 g of a yellow oil. The oil was recrystallized from isopropanol with the addition of one equivalent of fumaric acid to give 0.40 g of the (S)-enantiomer of the title compound as a pale yellow solid fumarate, sesquihydrate, m.p. 194–196° C.

Elemental Analysis for: C$_{25}$H$_{26}$N$_4$O$_3$.C$_4$H$_4$O$_4$.1.5 H$_2$O Calc'd: C, 60.72; H, 5.80; N, 9.77. Found: C, 60.90; H, 5.96; N, 9.63.

EXAMPLE 4

8-Methyl -2-(piperidin-1-ylmethyl)-2,3-dihydro[1,4]dioxino[2,3-f]quinoline (2R)-8-Methyl-2,3-dihydro[1,4]dioxino[2,3-f]quinolin-2-ylmethyl 4-methylbenzenesulfonate (0.75 g, 2.0 mmole) was dissolved in 10 mL of piperidine and heated at reflux under nitrogen for 6 hours. After cooling to room temperature, the mixture was concentrated to an oil in vacuum. The residue was column chromatographed on silica gel using 1% methanol in chloroform as eluant to give 0.41 g of a yellow oil. The oil was recrystallized from isopropanol with the addition of 1 mL of 4 N isopropanolic HCl to give 0.35 g of the (S)-enantiomer of the title compound as a yellow solid dihydrochloride, hemihydrate, m.p. 278–280° C.

Elemental Analysis for: C$_{18}$H$_{22}$N$_2$O$_2$.2HCl.0.5 H$_2$O Calc'd: C, 56.85; H, 6.83; N, 7.37. Found: C, 56.74; H, 6.65; N, 7.07.

EXAMPLE 5

(4-Fluorophenyl)(1-{[8-methyl-2,3-dihydro[1,4]dioxino[2,3-f]quinolin-2-yl]methyl}-4-piperidinyl)methanone (2R)-8-Methyl-2,3-dihydro[1,4]dioxino[2,3-f]quinolin-2-ylmethyl 4-methylbenzenesulfonate (0.75 g, 2.0 mmole) and 4-(4-fluorobenzoyl)-piperidine (1.0 g, 4.8 mmole) were combined in 10 mL of DMSO and heated at 80–90° C. under nitrogen for 6 hours. After cooling to room temperature, the mixture was partitioned between 400 mL of ethyl acetate and 400 mL of saturated sodium bicarbonate solution. The organic phase was removed, washed with 400 mL of water, dried over sodium sulfate, filtered and concentrated in vacuum. The residue was column chromatographed on silica gel using 0.5% methanol in chloroform as eluant to give 0.17 g of a yellow oil. The oil was recrystallized from ethanol with the addition of one equivalent of fumaric acid to give 0.18 g of the (S)-enantiomer of the title compound as an off-white solid fumarate, one-quarter hydrate, m.p. 206–207° C.

Elemental Analysis for: $C_{25}H_{25}FN_2O_3 \cdot C_4H_4O_4 \cdot 0.25\ H_2O$ Calc'd: C, 64.38; H, 5.50; N, 5.18. Found: C, 64.67; H, 5.55; N, 4.97.

EXAMPLE 6

1-{[8-Methyl-2,3-dihydro[1,4]dioxino[2,3-f] quinolin-2-yl]methyl}-4-[3-(trifluoromethyl) phenyl]-4-piperidinol (2R)-8-Methyl-2,3-dihydro[1,4]dioxino[2,3-f]quinolin-2-ylmethyl 4-methylbenzenesulfonate (0.75 g, 2.0 mmole) and 4-[(3-trifluoromethyl)phenyl]-4-hydroxypiperidine (1.0 g, 4.1 mmole) were combined in 10 mL of DMSO and heated at 80° C. under nitrogen for 6 hours. After cooling to room temperature, the mixture was partitioned between 400 mL of ethyl acetate and 300 mL of saturated sodium bicarbonate solution. The organic phase was removed, washed with 300 mL of water, dried over magnesium sulfate, filtered and concentrated in vacuum. The residue was column chromatographed on silica gel using 1% methanol in methylene chloride as eluant to give 0.57 g of a yellow oil. The oil was recrystallized from ethanol with the addition of one equivalent of fumaric acid to give 0.30 g of the (S)-enantiomer of the title compound as a pale yellow solid fumarate, three-quarter hydrate, m.p. 133–135° C.

Elemental Analysis for: $C_{25}H_{25}F_3N_2O_3 \cdot C_4H_4O_4 \cdot 0.75\ H_2O$ Calc'd: C, 59.23; H, 5.23; N, 4.76. Found: C, 59.12; H, 5.41; N, 4.47.

EXAMPLE 7

1-{[8-Methyl-2,3-dihydro[1,4]dioxino[2,3-f] quinolin-2-yl]methyl}-4-phenyl-4-piperidinecarbonitrile (2R)-8-Methyl-2,3-dihydro[1,4]dioxino[2,3-f]quinolin-2-ylmethyl 4-methylbenzenesulfonate (0.75 g, 2.0 mmole) and 4-phenyl-4-cyanopiperidine (1.0 g, 5.4 mmole) were combined in 10 mL of DMSO and heated at 80–90° C. under nitrogen for 6 hours. After cooling to room temperature, the mixture was partitioned between 400 mL of ethyl acetate and 300 mL of saturated sodium bicarbonate solution. The organic phase was removed, washed with 300 mL of water, dried over magnesium sulfate, filtered and concentrated in vacuum. The residue was column chromatographed on silica gel using 1% methanol in methylene chloride as eluant to give 250 mg of a yellow oil. The oil was recrystallized from ethanol with the addition of one equivalent of fumaric acid to give 0.19 g of the (S)-enantiomer of the title compound, m.p. 185–7° C.

Elemental Analysis for: $C_{25}H_{25}N_3O_2 \cdot C_4H_4O_4$ Calc'd: C, 67.56; H, 5.67; N, 8.15. Found: C, 67.24; H, 5.71; N, 8.00.

EXAMPLE 8

8-Methyl-2-{[4-phenyl-3,6-dihydro-1(2H)-pyridinyl] methyl}-2,3-dihydro[1,4]dioxino[2,3-f]quinoline (2R)-8-Methyl-2,3-dihydro[1,4]dioxino[2,3-f]quinolin-2-ylmethyl 4-methylbenzenesulfonate (0.75 g, 2.0 mmole) and 4-phenyl-1,2,3,6-tetrahydropyridine (1.0 g, 6.3 mmole) were combined in 10 mL of DMSO and heated at 80–90° C. under nitrogen for 6 hours. After cooling to room temperature, the mixture was partitioned between 400 mL of ethyl acetate and 400 mL of saturated sodium bicarbonate solution. The organic phase was removed, washed with 400 mL of water, dried over sodium sulfate, filtered and concentrated in vacuum. The residue was column chromatographed on silica gel using 0.5% methanol in methylene chloride as eluant to give 0.34 g of a yellow oil. The oil was recrystallized from ethanol with the addition of 0.15 g of fumaric acid to give 0.12 g of the (S)-enantiomer of the title compound as a white solid sesquifumarate, one-quarter hydrate, m.p. 185–188° C.

Elemental Analysis for: $C_{24}H_{24}N_2O_2 \cdot 1.5\ C_4H_4O_4 \cdot 0.25\ H_2O$ Calc'd: C, 65.39; H, 5.58; N, 5.08. Found: C, 65.26; H, 5.37; N, 5.08.

INTERMEDIATE 12

{7-Nitro-8-[(E)-3-oxo-1-pentenyl]-2,3-dihydro-1,4-benzodioxin-2-yl}methyl 4-methylbenzenesulfonate To a solution of 5.00 g (12.2 mmole) of [(2R)-8-formyl-7-nitro-2,3-dihydro-1,4-benzodioxin-2-yl]methyl 4-methylbenzenesulfonate in 200 mL of toluene was added 5.10 g (15.3 mmole) of 1-triphenylphosphoranylidene-2-butanone. The mixture was stirred at room temperature under nitrogen for 5 hours, after which time the solvent was removed in vacuum and the crude residue was column chromatographed on silica gel with methylene chloride as eluant to give 5.0 g of the (R)-enantiomer of the title compound as a yellow solid (m.p. 114° C.).

Elemental Analysis for: $C_{17}H_{15}NO_8S$ Calc'd: C, 56.37; H, 4.73; N, 3.13. Found: C, 56.81; H, 4.60; N, 3.01.

INTERMEDIATE 13

(8-Ethyl-2,3-dihydro[1,4]dioxino[2,3-f]quinolin-2-yl)methyl 4-methylbenzenesulfonate To a solution of {(2R)-7-nitro-8-[(E)-3-oxo-1-pentenyl]-2,3-dihydro-1,4-benzo-dioxin-2-yl}methyl 4-methylbenzenesulfonate (1.57 g, 3.50 mmole) in 100 mL of acetic acid/ethanol (1:1) was added 1.00 g (17.9 mmole) of iron powder and the mixture was heated at reflux under nitrogen for 8 hours. After the reaction was complete, 150 mL of water was added and the mixture filtered through a pad of celite. The filtrate was neutralized with saturated aqueous sodium bicarbonate and extracted with ethyl acetate. The extract was dried over magnesium sulfate, filtered and evaporated in vacuum. The residue was column chromatographed on silica gel using a gradient elution commencing with 20% ethyl acetate/hexane and ending with 70% ethyl acetate/hexane to give 0.94 g of the (R)-enantiomer of the title compound as a yellow oil. $^1$H-NMR (CDCl$_3$): doublet 8.2 δ (1 H); doublet 7.8 δ (2 H); doublet 7.55 δ (1 H); 7.2–7.3 δ (4 H); multiplet 4.6 δ (1 H); multiplet 4.2–4.4 δ (3 H); multiplet 4.1 δ (1 H); quartet 3.0 δ (2 H); singlet 2.4 δ (3 H); triplet 1.4 δ (3 H).

EXAMPLE 9

8-{[8-Ethyl-2,3-dihydro[1,4]dioxino[2,3-f]quinolin-2-yl]methyl}-1-phenyl-1,3,8-triazaspiro[4.5]decan-4-one (2R)-8-Ethyl-2,3-dihydro[1,4]dioxino[2,3-f]quinolin-2-ylmethyl 4-methylbenzenesulfonate (0.45 g, 1.1 mmole) and 1-phenyl-1,3,6-triazaspiro[4.5]decan-4-one (0.78 g, 3.4 mmole) were combined in 30 mL of DMSO and heated at 80° C. under nitrogen for 3 hours. After cooling to room temperature, the mixture was partitioned between 400 mL each of ethyl acetate and saturated sodium bicarbonate solution. The organic phase was removed, washed with saturated brine, dried over magnesium sulfate and concentrated to a brown oil in vacuum. This was column chromatographed on silica gel with 3% methanol in methylene chloride as eluant to give 0.31 g of a yellow oil. The oil was recrystallized from ethanol with the addition of 0.094 g of fumaric acid to give 0.10 g of the (S)-enantiomer of the title compound as a yellow solid fumarate, hemihydrate, m.p. 207–209° C.

Elemental Analysis for: $C_{27}H_{30}N_4O_3 \cdot C_4H_4O_4 \cdot 0.5\ H_2O$
Calc'd: C, 63.80; H, 6.04; N, 9.60. Found: C, 63.82; H, 5.81; N, 9.36.

What is claimed is:

1. A compound of formula I

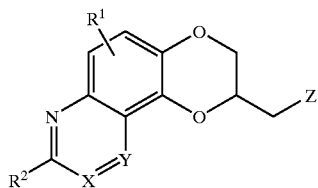

(I)

wherein
$R^1$ is hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$ is hydrogen, hydroxy, halo, amino, mono- or di-alkylamino in which each alkyl group has 1 to 6 carbon atoms, or alkyl of one to six carbon atoms;

X is N or $CR^3$;
Y is N or CH;
$R^3$ is hydrogen or alkyl of one to six carbon atoms;
Z is pyrrolidinyl, piperidinyl, homopiperidinyl, morpholinyl, thiomorpholinyl,

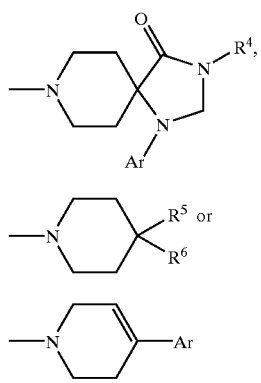

$R^4$ is hydrogen, alkyl of 1 to 6 carbon atoms, alkenyl of 3 to 6 carbon atoms or alkynyl or 3 to 6 carbon atoms;
Ar is phenyl, naphthyl, pyridinyl, pyrimidinyl, pyrazinyl, furyl, or thienyl;

$R^5$ is hydroxy, cyano or carboxamido and $R^6$ is Ar; or
$R^5$ is hydrogen and $R^6$ is benzoyl, 1-benzimidazol-2-onyl, benzoisothiazolyl, benzisoxazolyl, or —$(CH_2)_mQ$;
m is 0 to 4; and
Q is Ar,

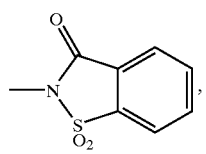

V

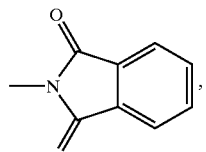

VI

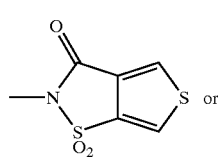

VII

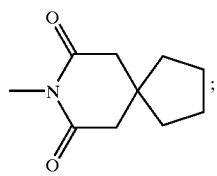

VIII or a pharmaceutically acceptable salt thereof;
wherein said phenyl, naphthyl, pyridinyl, pyrimidinyl, pyrazinyl, furyl, thienyl, 1-benzimidazol-2-onyl, benzoisothiazolyl, or benzisoxazolyl groups are optionally substituted with substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

2. A compound of claim 1 wherein $R^1$ is hydrogen, halo, trifluoromethyl, alkyl of one to six carbon atoms, alkoxy of one to six carbon atoms, amino, monoalkylamino of one to six carbon atoms or dialkylamino in which each alkyl group has one to six carbon atoms.

3. A compound of claim 1 wherein $R^1$ is hydrogen, halo, trifluoromethyl, alkyl of one to six carbon atoms or alkoxy of one to six carbon atoms.

4. A compound of claim 1 wherein $R^2$ is hydrogen, amino, monoalkylamino of one to six carbon atoms, dialkylamino in which each alkyl group has one to six carbon atoms, or alkyl of one to six carbon atom.

5. A compound of claim 1 wherein $R^2$ is hydrogen, or alkyl of one to six carbon atom.

6. A compound of claim 1 wherein X and Y are each CH.

7. A compound of claim 1 wherein Z is a radical of formula II or III.

8. A compound of claim 7 wherein $R^1$ is hydrogen, halo, trifluoromethyl, alkyl of one to six carbon atoms, alkoxy of one to six carbon atoms, amino, mono- or di-alkylamino in which each alkyl group has one to six carbon atoms; $R^2$ is hydrogen, amino, mono- or di-alkylamino in which each alkyl group has one to six carbon atoms, or alkyl of one to six carbon atom, and Z is a radical of formula II.

9. A compound of claim 8 wherein R¹ is hydrogen, halo, trifluoromethyl, alkyl of one to six carbon atoms or alkoxy of one to six carbon atoms; R² is hydrogen, or alkyl of one to six carbon atom, and X and Y are CH.

10. A compound of claim 7 wherein R¹ is hydrogen, halo, trifluoromethyl, alkyl of one to six carbon atoms, alkoxy of one to six carbon atoms, amino, mono- or di-alkylamino in which each alkyl group has one to six carbon atoms; R² is hydrogen, amino, mono- or di-alkylamino in which each alkyl group has one to six carbon atoms, or alkyl of one to six carbon atom, and Z is a radical of formula III, R⁵ is hydroxy and R⁶ is Ar; or R⁵ is hydrogen and R⁶ is benzoyl, 1-benzimidazol-2-onyl, benzoisothiazolyl, benzisoxazolyl, each optionally substituted, or —(CH₂)ₘQ.

11. A compound of claim 10 wherein R¹ is hydrogen, halo, trifluoromethyl, alkyl of one to six carbon atoms or alkoxy of one to six carbon atoms; R² is hydrogen, or alkyl of one to six carbon atom, X and Y are CH; and m is 0 or 1.

12. A compound of claim 1 wherein R¹ is hydrogen, halo, trifluoromethyl, alkyl of one to six carbon atoms, alkoxy of one to six carbon atoms, amino, mono- or di-alkylamino in which each alkyl group has one to six carbon atoms; R² is hydrogen, amino, mono- or di-alkylamino in which each alkyl group has one to six carbon atoms, or alkyl of one to six carbon atom, and Z is a radical of formula IV.

13. A compound of claim 12 wherein R¹ is hydrogen, halo, trifluoromethyl, alkyl of one to six carbon atoms or alkoxy of one to six carbon atoms; R² is hydrogen, or alkyl of one to six carbon atom and X and Y are CH.

14. The compound of claim 1 which is 8-[2,3-dihydro[1,4]dioxino[2,3-f]quinolin-2-ylmethyl]-1-phenyl-1,3,8-triazaspiro[4.5]decan-4-one or a pharmaceutically acceptable salt thereof.

15. The compound of claim 1 which is 8-{[8-methyl-2,3-dihydro[1,4]dioxino[2,3-f]quinolin-2-yl]methyl}-1-phenyl-1,3,8-triazaspiro[4.5]decan-4-one or a pharmaceutically acceptable salt thereof.

16. The compound of claim 1 which is 1-(1-{[8-methyl-2,3-dihydro[1,4]-dioxino[2,3-f]quinolin-2-yl]methyl}piperidin-4-yl)-1,3-dihydro-2H-benzimidazol-2-one or a pharmaceutically acceptable salt thereof.

17. The compound of claim 1 which is 8-methyl-2-(piperidin-1-ylmethyl)-2,3-dihydro[1,4]dioxino[2,3-f]quinoline or a pharmaceutically acceptable salt thereof.

18. The compound of claim 1 which is (4-fluorophenyl)(1-{[8-methyl-2,3-dihydro[1,4]dioxino[2,3-f]quinolin-2-yl]methyl}-4-piperidinyl)methanone or a pharmaceutically acceptable salt thereof.

19. The compound of claim 1 which is 1-{[8-methyl-2,3-dihydro[1,4]-dioxino-[2,3-f]-quinolin-2-yl]methyl}-4-[3-(trifluoromethyl)phenyl]-4piperidinol or a pharmaceutically acceptable salt thereof.

20. The compound of claim 1 which is 1-{[8-methyl-2,3-dihydro[1,4]-dioxino[2,3-f]quinolin-2-yl]methyl}-4-phenyl-4-piperidinecarbonitrile or a pharmaceutically acceptable salt thereof.

21. The compound of claim 1 which is 8-methyl-2-{[4-phenyl-3,6-dihydro-1-(2H)-pyridinyl]methyl}-2,3-dihydro[1,4]dioxino[2,3-f]quinoline or a pharmaceutically acceptable salt thereof.

22. The compound of claim 1 which is 8-{[8-ethyl-2,3-dihydro[1,4]dioxino-[2,3-f]-quinolin-2-yl]methyl}-1-phenyl-1,3,8-triazaspiro[4.5]decan-4-one or a pharmaceutically acceptable salt thereof.

23. A method of treating a subject suffering from a condition selected from the group consisting of anxiety, aggression and stress which comprises providing to the subject suffering from said condition, a therapeutically effective amount of a compound of formula I

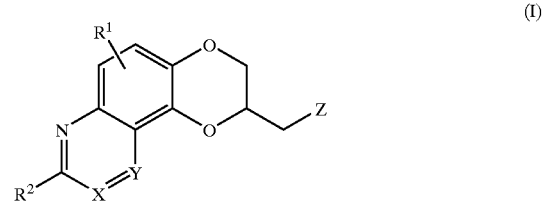

(I)

wherein

R¹ is hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

R² is hydrogen, hydroxy, halo, amino, mono- or di-alkylamino in which each alkyl group has 1 to 6 carbon atoms, or alkyl of one to six carbon atoms;

X is N or CR³;

Y is N or CH;

R³ is hydrogen or alkyl of one to six carbon atoms;

Z is pyrrolidinyl, piperidinyl, homopiperidinyl, morpholinyl, thiomorpholinyl,

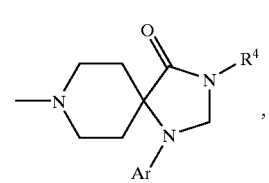

II

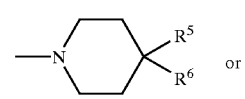

III or

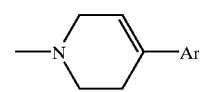

IV

R⁴ is hydrogen, alkyl of 1 to 6 carbon atoms, alkenyl of 3 to 6 carbon atoms or alkynyl or 3 to 6 carbon atoms;

Ar is phenyl, naphthyl, pyridinyl, pyrimidinyl, pyrazinyl, furyl, or thienyl;

R⁵ is hydroxy, cyano or carboxamido and R⁶ is Ar; or

R⁵ is hydrogen and R⁶ is benzoyl, 1-benzimidazol-2-onyl, benzoisothiazolyl, benzisoxazolyl, or —(CH₂)ₘQ;

m is 0 to 4; and

Q is Ar,

V

VI

VII  or

VIII or a pharmaceutically acceptable salt thereof;
wherein said phenyl, naphthyl, pyridinyl, pyrimidinyl, pyrazinyl, furyl, thienyl, 1-benzimidazol-2-onyl, benzoisothiazolyl, or benzisoxazolyl groups are optionally substituted with substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

24. The method of claim 23 wherein the subject is a human.

25. A method of treating a subject suffering from a condition selected from the group consisting of eating disorders, disorders of thermoregulation, sleep dysfunction and sexual dysfunction which comprises providing to the subject suffering from said condition, a therapeutically effective amount of a compound of formula I (I)

wherein
$R^1$ is hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$ is hydrogen, hydroxy, halo, amino, mono- or di-alkylamino in which each alkyl group has 1 to 6 carbon atoms, or alkyl of one to six carbon atoms;
X is N or $CR^3$;
Y is N or CH;
$R^3$ is hydrogen or alkyl of one to six carbon atoms;
Z is pyrrolidinyl, piperidinyl, homopiperidinyl, morpholinyl, thiomorpholinyl,

II

III  or

IV $R^4$ is hydrogen, alkyl of 1 to 6 carbon atoms, alkenyl of 3 to 6 carbon atoms or alkynyl or 3 to 6 carbon atoms;
Ar is phenyl, naphthyl, pyridinyl, pyrimidinyl, pyrazinyl, furyl, or thienyl;
$R^5$ is hydroxy, cyano or carboxamido and $R^6$ is Ar; or
$R^5$ is hydrogen and $R^6$ is benzoyl, 1-benzimidazol-2-onyl, benzoisothiazolyl, benzisoxazolyl, or —$(CH_2)_m$Q;
m is 0 to 4; and
Q is Ar,

V

VI

VII  or

VIII or a pharmaceutically acceptable salt thereof;
wherein said phenyl, naphthyl, pyridinyl, pyrimidinyl, pyrazinyl, furyl, thienyl, 1-benzimidazol-2-onyl, benzoisothiazolyl, or benzisoxazolyl groups are optionally substituted with substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

26. The method of claim 25 wherein the subject is a human.

27. A method of treating a subject suffering depression comprising providing to the subject suffering from said condition, an antidepressant amount of a serotonin selective reuptake inhibitor and an amount of a compound of formula I

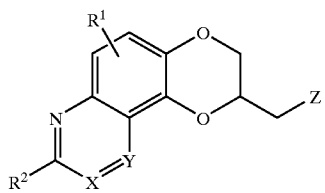
(I)

wherein
R$^1$ is hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

R$^2$ is hydrogen, hydroxy, halo, amino, mono- or di-alkylamino in which each alkyl group has 1 to 6 carbon atoms, or alkyl of one to six carbon atoms;

X is N or CR$^3$;
Y is N or CH;
R$^3$ is hydrogen or alkyl of one to six carbon atoms;
Z is pyrrolidinyl, piperidinyl, homopiperidinyl, morpholinyl, thiomorpholinyl,

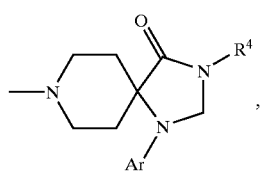
II

III

IV

R$^4$ is hydrogen, alkyl of 1 to 6 carbon atoms, alkenyl of 3 to 6 carbon atoms or alkynyl or 3 to 6 carbon atoms;
Ar is phenyl, naphthyl, pyridinyl, pyrimidinyl, pyrazinyl, furyl, or thienyl;
R$^5$ is hydroxy, cyano or carboxamido and R$^6$ is Ar; or
R$^5$ is hydrogen and R$^6$ is benzoyl, 1-benzimidazol-2-onyl, benzoisothiazolyl, benzisoxazolyl, or —(CH$_2$)$_m$Q;

m is 0 to 4; and
Q is Ar,

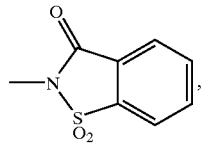
V

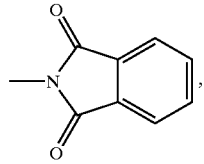
VI

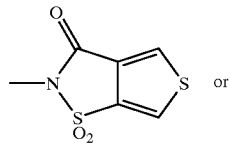
VII or

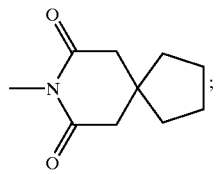
VIII or a pharmaceutically acceptable salt thereof,
wherein said phenyl, naphthyl, pyridinyl, pyrimidinyl, pyrazinyl, furyl, thienyl, 1-benzimidazol-2-onyl, benzoisothiazolyl, or benzisoxazolyl groups are optionally substituted with substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;
said amount of compound of Formula I being effective to increase the onset of antidepressant efficacy.

28. The method of claim 27 wherein the subject is a human.

29. The method of claim 27 wherein the serotonin selective reuptake inhibitor is sertraline, fluvoxamine, paroxetine, venlafaxine, duloxetine, citalopram, fluoxetine or metabolites thereof.

30. A pharmaceutical composition comprising a therapeutically effective amount of a compound of formula I

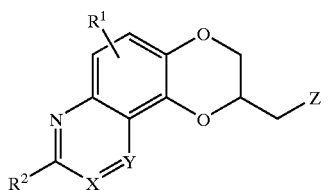
(I)

wherein
R$^1$ is hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$ is hydrogen, hydroxy, halo, amino, mono- or di-alkylamino in which each alkyl group has 1 to 6 carbon atoms, or alkyl of one to six carbon atoms;

X is N or $CR^3$;

Y is N or CH;

$R^3$ is hydrogen or alkyl of one to six carbon atoms;

Z is pyrrolidinyl, piperidinyl, homopiperidinyl, morpholinyl, thiomorpholinyl,

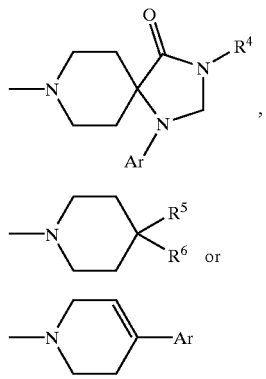

$R^4$ is hydrogen, alkyl of 1 to 6 carbon atoms, alkenyl of 3 to 6 carbon atoms or alkynyl or 3 to 6 carbon atoms;

Ar is phenyl, naphthyl, pyridinyl, pyrimidinyl, pyrazinyl, furyl, or thienyl $R^5$ is hydroxy, cyano or carboxamido and $R^6$ is Ar; or $R^5$ is hydrogen and $R^6$ is benzoyl, 1-benzimidazol-2-onyl, benzoisothiazolyl, benzisoxazolyl, or —$(CH_2)_mQ$;

m is 0 to 4; and

Q is Ar,

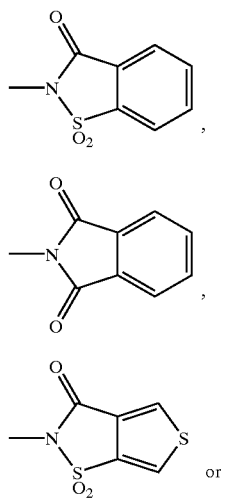

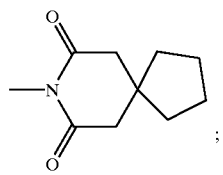

or a pharmaceutically acceptable salt thereof, wherein said phenyl, naphthyl, pyridinyl, pyrimidinyl, pyrazinyl, furyl thienyl, 1-benzimidazol-2-onyl, benzoisothiazolyl, or benzisoxazolyl groups are optionally substituted with substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

and a pharmaceutically acceptable carrier or excipient.

31. The composition of claim 30 further comprising an antidepressant amount of a serotonin selective reuptake inhibitor.

32. The composition of claim 31 wherein the selective reuptake inhibitor is sertraline, fluvoxamine, paroxetine, venlafaxine, duloxetine, citalopram, fluoxetine or metabolites thereof.

33. A compound of claim 1 wherein at least one of said phenyl, naphthyl, pyridinyl, pyrimidinyl, pyrazinyl, furyl, thienyl, 1-benzimidazol-2-onyl, benzoisothiazolyl, or benzisoxazolyl, bears 1 to 3 substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

34. A compound of claim 23 wherein at least one of said phenyl, naphthyl, pyridinyl, pyrimidinyl, pyrazinyl, furyl, thienyl, 1-benzimidazol-2-onyl, benzoisothiazolyl, or benzisoxazolyl, bears 1 to 3 substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

35. A compound of claim 25 wherein at least one of said phenyl, naphthyl, pyridinyl, pyrimidinyl, pyrazinyl, furyl, thienyl, 1-benzimidazol-2-onyl, benzoisothiazolyl, or benzisoxazolyl, bears 1 to 3 substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

36. A compound of claim 27 wherein at least one of said phenyl, naphthyl, pyridinyl, pyrimidinyl, pyrazinyl, furyl, thienyl, 1-benzimidazol-2-onyl, benzoisothiazolyl, or benzisoxazolyl, bears 1 to 3 substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

37. A compound of claim 30 wherein at least one of said phenyl, naphthyl, pyridinyl, pyrimidinyl, pyrazinyl, furyl, thienyl, 1-benzimidazol-2-onyl, benzoisothiazolyl, or benzisoxazolyl, bears 1 to 3 substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

\* \* \* \* \*